(12) United States Patent
Schultheis et al.

(10) Patent No.: US 11,419,657 B2
(45) Date of Patent: Aug. 23, 2022

(54) COMPENSATION ASSEMBLY FOR FLUID INJECTION LINE OF INTRAVASCULAR CATHETER SYSTEM

(71) Applicant: Cryterion Medical, Inc., Carlsbad, CA (US)

(72) Inventors: Eric A. Schultheis, San Clemente, CA (US); Eugene J. Jung, San Diego, CA (US); Xiaoyu Yu, San Diego, CA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 630 days.

(21) Appl. No.: 16/206,308

(22) Filed: Nov. 30, 2018

(65) Prior Publication Data

US 2019/0167331 A1 Jun. 6, 2019

Related U.S. Application Data

(60) Provisional application No. 62/617,979, filed on Jan. 16, 2018, provisional application No. 62/615,362, (Continued)

(51) Int. Cl.
*A61B 18/02* (2006.01)
*A61B 18/00* (2006.01)
*A61M 25/09* (2006.01)

(52) U.S. Cl.
CPC ...... *A61B 18/02* (2013.01); *A61B 2018/0022* (2013.01); *A61B 2018/00166* (2013.01); (Continued)

(58) Field of Classification Search
CPC .......... A61B 18/02; A61B 2018/00166; A61B 2018/0022; A61B 2018/0212; A61B 2018/0262; A61B 2018/0287
See application file for complete search history.

(56) References Cited

U.S. PATENT DOCUMENTS

| 5,330,471 A | * | 7/1994 | Eggers | G02B 6/0096 |
| | | | | 606/48 |
| 6,551,309 B1 | * | 4/2003 | LePivert | A61B 18/02 |
| | | | | 606/20 |

(Continued)

FOREIGN PATENT DOCUMENTS

EP 2902070 A1 8/2015
EP 3120792 A1 1/2017

OTHER PUBLICATIONS

International Search Report and Written Opinion issued in PCT/US2018/063396, dated Mar. 13, 2019, 24 pages.

*Primary Examiner* — Daniel W Fowler
(74) *Attorney, Agent, or Firm* — Nelson Mullins Riley & Scarborough LLP; Brian W. Oberst; Jason R. Kraus

(57) ABSTRACT

A fluid injection line compensation assembly for an intravascular catheter system including a balloon catheter having a guidewire lumen and a cryoballoon, includes a fluid injection line, a proximal fluid injection line stop, and a distal fluid injection line stop. The fluid injection line has a fluid discharge region positioned within the cryoballoon. The fluid discharge region includes a fluid port so that cryogenic fluid can be distributed from the fluid injection line to within the cryoballoon. The fluid discharge region is not affixed to the guidewire lumen. The proximal fluid injection line stop is positioned adjacent to the guidewire lumen, the proximal fluid injection line stop being positioned within the cryoballoon. The distal fluid injection line stop is positioned adjacent to the guidewire lumen so that the fluid discharge region is positioned between the proximal fluid injection line stop and the distal fluid injection line stop.

13 Claims, 7 Drawing Sheets

Related U.S. Application Data filed on Jan. 9, 2018, provisional application No. 62/593,164, filed on Nov. 30, 2017.

(52) U.S. Cl.
CPC .............. *A61B 2018/0212* (2013.01); *A61B 2018/0262* (2013.01); *A61B 2018/0287* (2013.01); *A61M 2025/09125* (2013.01)

(56) References Cited

U.S. PATENT DOCUMENTS

| | | | |
|---|---|---|---|
| 7,220,257 B1 * | 5/2007 | Lafontaine | A61B 18/02 606/21 |
| 2002/0151880 A1 * | 10/2002 | Lafontaine | A61B 18/02 606/21 |
| 2002/0183731 A1 * | 12/2002 | Holland | A61B 18/0218 606/21 |
| 2004/0044334 A1 | 3/2004 | Lafontaine | |
| 2008/0004652 A1 * | 1/2008 | Abboud | A61M 25/10181 606/192 |
| 2011/0264086 A1 * | 10/2011 | Ingle | A61B 18/1492 606/33 |
| 2012/0101485 A1 | 4/2012 | Wittenberger | |
| 2015/0209100 A1 * | 7/2015 | Ineson | A61B 18/1402 606/42 |

* cited by examiner

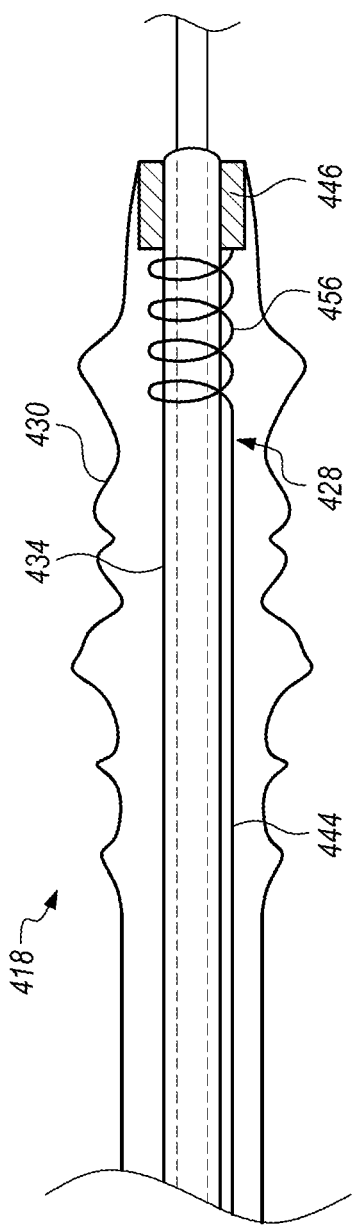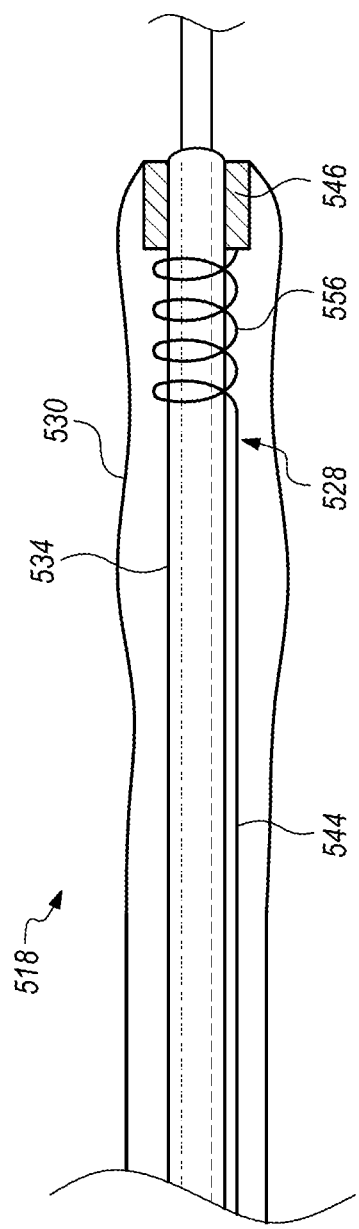

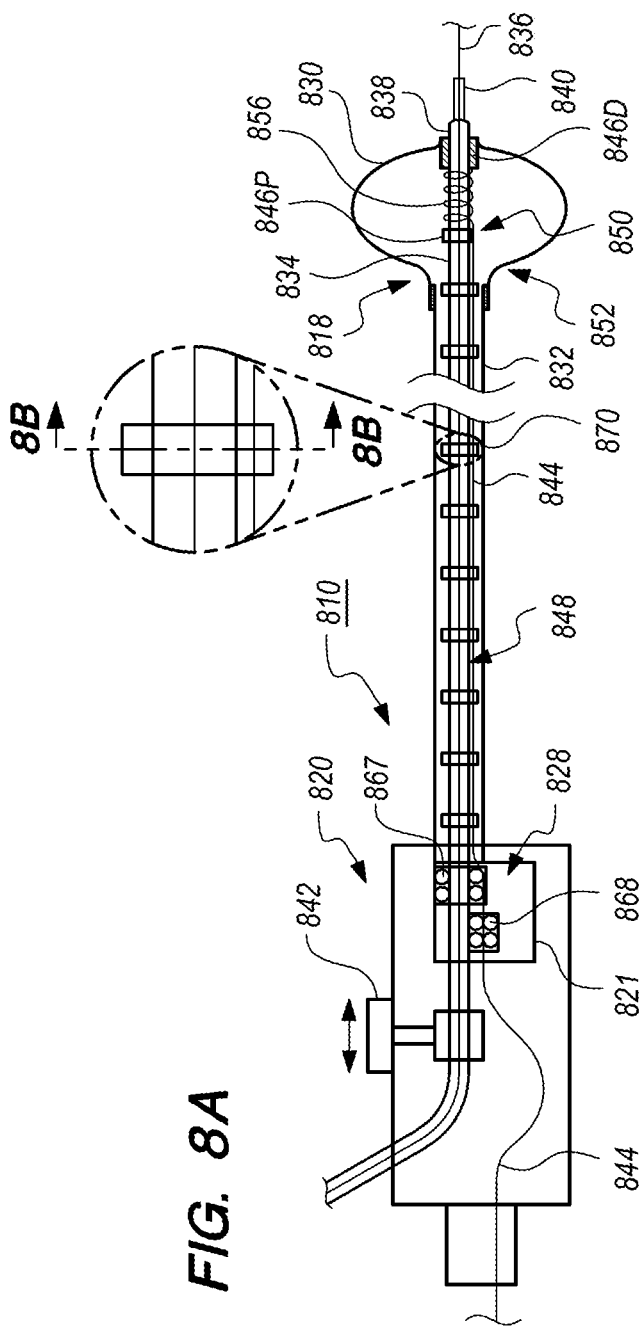

COMPENSATION ASSEMBLY FOR FLUID INJECTION LINE OF INTRAVASCULAR CATHETER SYSTEM

RELATED APPLICATIONS

This application claims priority on U.S. Provisional Application Ser. No. 62/593,164, filed on Nov. 30, 2017, and entitled "CRYOGENIC FLUID INJECTION LINE COMPENSATION ASSEMBLY"; U.S. Provisional Application Ser. No. 62/615,362, filed on Jan. 9, 2018, and entitled "CRYOGENIC FLUID INJECTION LINE COMPENSATION ASSEMBLY"; and U.S. Provisional Application Ser. No. 62/617,979, filed on Jan. 16, 2018, and entitled "CRYOGENIC FLUID INJECTION LINE COMPENSATION ASSEMBLY". As far as permitted, the contents of U.S. Provisional Application Ser. Nos. 62/593,164, 62/615,362, and 62/617,979 are incorporated in their entirety herein by reference.

BACKGROUND

Cardiac arrhythmias involve an abnormality in the electrical conduction of the heart and are a leading cause of stroke, heart disease, and sudden cardiac death. Treatment options for patients with arrhythmias include medications and/or the use of medical devices, which can include implantable devices and/or catheter ablation of cardiac tissue, to name a few.

In particular, catheter ablation involves delivering ablative energy to tissue inside the heart to block aberrant electrical activity from depolarizing heart muscle cells out of synchrony with the heart's normal conduction pattern. The procedure is performed by positioning the tip of an energy delivery catheter adjacent to diseased or targeted tissue in the heart. The energy delivery component of the system is typically at or near the most distal (i.e. farthest from the user or operator) portion of the catheter, and often at the tip of the catheter. Various forms of energy can be used to ablate diseased heart tissue. These can include cryoablation procedures which use cryogenic fluid within cryoballoons (also sometimes referred to herein as "cryogenic balloons" or "balloon catheters"), radio frequency (RF), ultrasound and laser energy, to name a few.

Atrial fibrillation (AF) is one of the most common arrhythmias treated using catheter ablation. AF is typically treated by pulmonary vein isolation, a procedure that removes unusual electrical conductivity in the pulmonary vein. In the earliest stages of the disease, paroxysmal AF, the treatment strategy involves isolating the pulmonary veins from the left atrial chamber. The objective of any device for the treatment of AF is to achieve isolation in all, not just some, of the pulmonary veins. Also, it is understood that complete occlusion of each pulmonary vein with the cryogenic balloon is required for adequate antral ablation and electrical isolation. Without pulmonary vein occlusion, blood flow over the balloon during ablation decreases the likelihood of sufficient lesion formation.

Cryoballoon ablation (or "cryoablation") procedures to treat atrial fibrillation have increased in use in the last several years. In part, this stems from the ease of use, shorter procedure times and improved patient outcomes that are possible through the use of cryoballoon ablation procedures. Despite these advantages, there remains needed improvement to further improve patient outcomes and to better facilitate real-time physiological monitoring of tissue to optimally titrate energy to perform both reversible "ice mapping" and permanent tissue ablation.

During a cryoablation procedure, with the aid of a guide wire, the distal tip of the catheter is positioned adjacent to targeted cardiac tissue. More specifically, during the specific use of cryoballoon ablation procedures, one or more cryoballoons are maneuvered through the vascular system of the patient, and are ultimately positioned near or against the targeted cardiac tissue. Once in position, the cryoballoons are inflated. Energy in the form of cryogenic fluid, such as liquid nitrous oxide or liquid nitrogen, is delivered through a fluid injection line to an interior of the inflated cryoballoon(s) to cause tissue necrosis of the targeted cardiac tissue, which renders the tissue incapable of conducting electrical signals. Once the targeted cardiac tissue has been necrosed, the cryoballoons are then deflated and the balloon catheter is removed from the patient's body.

The dose of energy delivered is a critical factor in increasing the likelihood that the treated tissue is permanently incapable of conduction. At the same time, delicate collateral tissue, such as the esophagus, the bronchus, and the phrenic nerve surrounding the ablation zone can be damaged and can lead to undesired complications. Thus, the operator must finely balance delivering therapeutic levels of energy to achieve intended tissue necrosis while avoiding excessive energy leading to collateral tissue injury.

Conventional fluid injection lines utilized during cryoballoon ablation procedures can have a coiled structure at the distal end. This coil is typically fastened onto a guidewire lumen with fluid exit ports located in a distal region of the balloon that is intended to contact the targeted cardiac tissue. These fluid exit ports enable the cryogenic fluid to exit the fluid injection line onto an inner surface of the cryoballoon. The guidewire lumen is often movable to help retract the cryoballoon into a catheter sheath to remove the entire catheter from the body after the cryoablation procedure has been completed. The movable guidewire lumen creates a need to extend and retract the fluid injection line in concert with the guidewire lumen. Current state of the art devices utilize relatively complex compensatory systems to perform this function. Additionally, the noted components of the fluid injection line can be relatively expensive components requiring exacting processes to ensure proper port diameter, shape and positioning.

Unfortunately, a fluid injection line that is immovably affixed to a distal segment of the guidewire lumen may impart unwanted forces which can bow and distort the guidewire lumen. This, in turn, can malposition the fluid injection line and its ports with respect to the cryoballoon. As a result, the distribution of the cryogenic fluid onto the surface of the cryoballoon may not be uniform, causing an undesirable temperature variation on the inner surface of the cryoballoon and potentially compromising procedural outcomes.

Moreover, some conventional devices utilize a bellow to seal around the guidewire lumen during extension (deflation) and retraction (inflation) of the cryoballoon. The bellow accommodates the range of guidewire movement due to its accordion design. Consequently, the bellow design can also result in a bias force on the guidewire lumen to maintain the seal around the guidewire lumen during extension and retraction of the cryoballoon. This biasing force can cause an unpredictable and unwanted movement on the guidewire lumen during the ablation procedure.

SUMMARY

The present invention is directed toward a fluid injection line compensation assembly for an intravascular catheter system, the intravascular catheter system including a balloon catheter having a guidewire lumen and a cryoballoon. In various embodiments, the fluid injection line compensation assembly includes a fluid injection line, a proximal fluid injection line stop, and a distal fluid injection line stop. The fluid injection line has a fluid discharge region positioned within the cryoballoon. The fluid discharge region includes a fluid port so that cryogenic fluid can be distributed from the fluid injection line to within the cryoballoon. The fluid discharge region is not affixed to the guidewire lumen. The proximal fluid injection line stop is positioned adjacent to the guidewire lumen, the proximal fluid injection line stop being positioned within the cryoballoon. The distal fluid injection line stop is positioned adjacent to the guidewire lumen so that the fluid discharge region is positioned between the proximal fluid injection line stop and the distal fluid injection line stop.

In some embodiments, the fluid discharge region is movable relative to the guidewire lumen. In one such embodiment, the fluid discharge region is movable in a longitudinal direction along the guidewire lumen. In another such embodiment, the fluid discharge region is rotatably movable about the guidewire lumen.

Additionally, in certain embodiments, the fluid injection line compensation assembly further includes a frictional element that frictionally maintains the positioning of the fluid injection line absent movement of the guidewire lumen. In some such embodiments, when the guidewire lumen moves in either a distal or proximal direction, the fluid injection line moves substantially with the guidewire lumen. In certain non-exclusive alternative embodiments, the frictional element can include one or more O-rings, an electronic actuator, a solenoid, or a set screw. Further, in some embodiments, the frictional element can be tuned to vary an amount of friction between the frictional element and the fluid injection line.

The intravascular catheter system can further include a handle assembly. In some embodiments, the frictional element is positioned within the handle assembly. Additionally, the handle assembly can further include a guidewire lumen sealer that encircles at least a portion of the guidewire lumen and forms a seal around the guidewire lumen.

Further, in certain embodiments, the balloon catheter further includes a coupler that holds a portion of the fluid injection line adjacent to a portion of the guidewire lumen. In one such embodiment, the coupler at least partially encircles the fluid injection line and the guidewire lumen.

Additionally, in some embodiments, at least one of the proximal fluid injection line stop and the distal fluid injection line stop encircles the guidewire lumen and/or is secured to the guidewire lumen.

In another application, the present invention is also directed toward a handle assembly for an intravascular catheter system, the intravascular catheter system including a guidewire lumen and a cryoballoon, the handle assembly including a guidewire lumen sealer that encircles at least a portion of the guidewire lumen and forms a seal around the guidewire lumen. In some embodiments, the guidewire lumen sealer does not bias the guidewire lumen in either a proximal or a distal direction relative to the cryoballoon. The guidewire lumen sealer can come in any suitable form such as an O-ring, a plurality of O-rings, an electronic actuator, a solenoid, a set screw, or another suitable form.

Additionally, the present invention is directed toward an intravascular catheter system including a balloon catheter having a guidewire lumen and a cryoballoon, a fluid injection line compensation assembly, and a handle assembly; wherein the fluid injection line compensation assembly is configured to compensate for changes in positioning of the guidewire lumen during operation of the intravascular catheter system.

In still another application, the present invention is directed toward a fluid injection line compensation assembly for an intravascular catheter system, the intravascular catheter system including a handle assembly and a balloon catheter having a cryoballoon, the fluid injection line compensation assembly including (i) a fluid injection line having a distal region positioned within the cryoballoon, the distal region including a fluid discharge region having a fluid port so that cryogenic fluid can be distributed from the fluid injection line to within the cryoballoon; (ii) a fluid injection line stop that is positioned within the cryoballoon; (iii) a distal bias stop that is secured to the fluid injection line; and (iv) a fluid injection line bias that imparts a bias force upon the distal bias stop to bias the fluid injection line in a direction toward the fluid injection line stop.

Additionally, in yet another application, the present invention is further directed toward a fluid injection line compensation assembly for an intravascular catheter system, the intravascular catheter system including a balloon catheter having a cryoballoon, the fluid injection line compensation assembly including a fluid injection line having a distal region and a proximal region, the distal region being positioned within the cryoballoon, the distal region including a fluid discharge region having a fluid port so that cryogenic fluid can be distributed from the fluid injection line to within the cryoballoon, the proximal region being configured to form a compression spring that biases the distal region in a direction away from the proximal region.

BRIEF DESCRIPTION OF THE DRAWINGS

The novel features of this invention, as well as the invention itself, both as to its structure and its operation, will be best understood from the accompanying drawings, taken in conjunction with the accompanying description, in which similar reference characters refer to similar parts, and in which:

FIG. 4 is a simplified schematic side view illustration of a portion of one embodiment of the balloon catheter illustrated in a deflated state, and a portion of an embodiment of the fluid injection line compensation assembly;

FIG. 5 is a simplified schematic side view illustration of a portion of one embodiment of the balloon catheter illustrated in an extended state, and a portion of an embodiment of the fluid injection line compensation assembly;

FIG. 8A is a simplified schematic side view illustration of a portion of yet another embodiment of the intravascular catheter system, including the balloon catheter and yet another embodiment of the fluid injection line compensation assembly;

FIG. 8B is a simplified schematic cross-sectional view illustration of a portion of the balloon catheter taken on line 8B-8B in FIG. 8A;

DESCRIPTION

Embodiments of the present invention are described herein in the context of a fluid injection line compensation assembly (sometimes referred to herein simply as a "compensation assembly") for a fluid injection line of an intravascular catheter system. More specifically, as provided herein, the compensation assembly is uniquely configured to compensate for necessary changes in length and/or positioning of a guidewire lumen during operation of the intravascular catheter system such that the fluid injection line is extended and retracted in concert with the extension and retraction of the guidewire lumen.

Those of ordinary skill in the art will realize that the following detailed description of the present invention is illustrative only and is not intended to be in any way limiting. Other embodiments of the present invention will readily suggest themselves to such skilled persons having the benefit of this disclosure. Reference will now be made in detail to implementations of the present invention as illustrated in the accompanying drawings.

In the interest of clarity, not all of the routine features of the implementations described herein are shown and described. It will, of course, be appreciated that in the development of any such actual implementation, numerous implementation-specific decisions must be made in order to achieve the developer's specific goals, such as compliance with application-related and business-related constraints, and that these specific goals will vary from one implementation to another and from one developer to another. Moreover, it will be appreciated that such a development effort might be complex and time-consuming, but would nevertheless be a routine undertaking of engineering for those of ordinary skill in the art having the benefit of this disclosure.

Although the disclosure provided herein focuses mainly on cryogenics, it is understood that various other forms of energy can be used to ablate diseased heart tissue. These can include radio frequency (RF), ultrasound and laser energy, as non-exclusive examples. The present invention is intended to be effective with any or all of these and other forms of energy.

Figure 1:
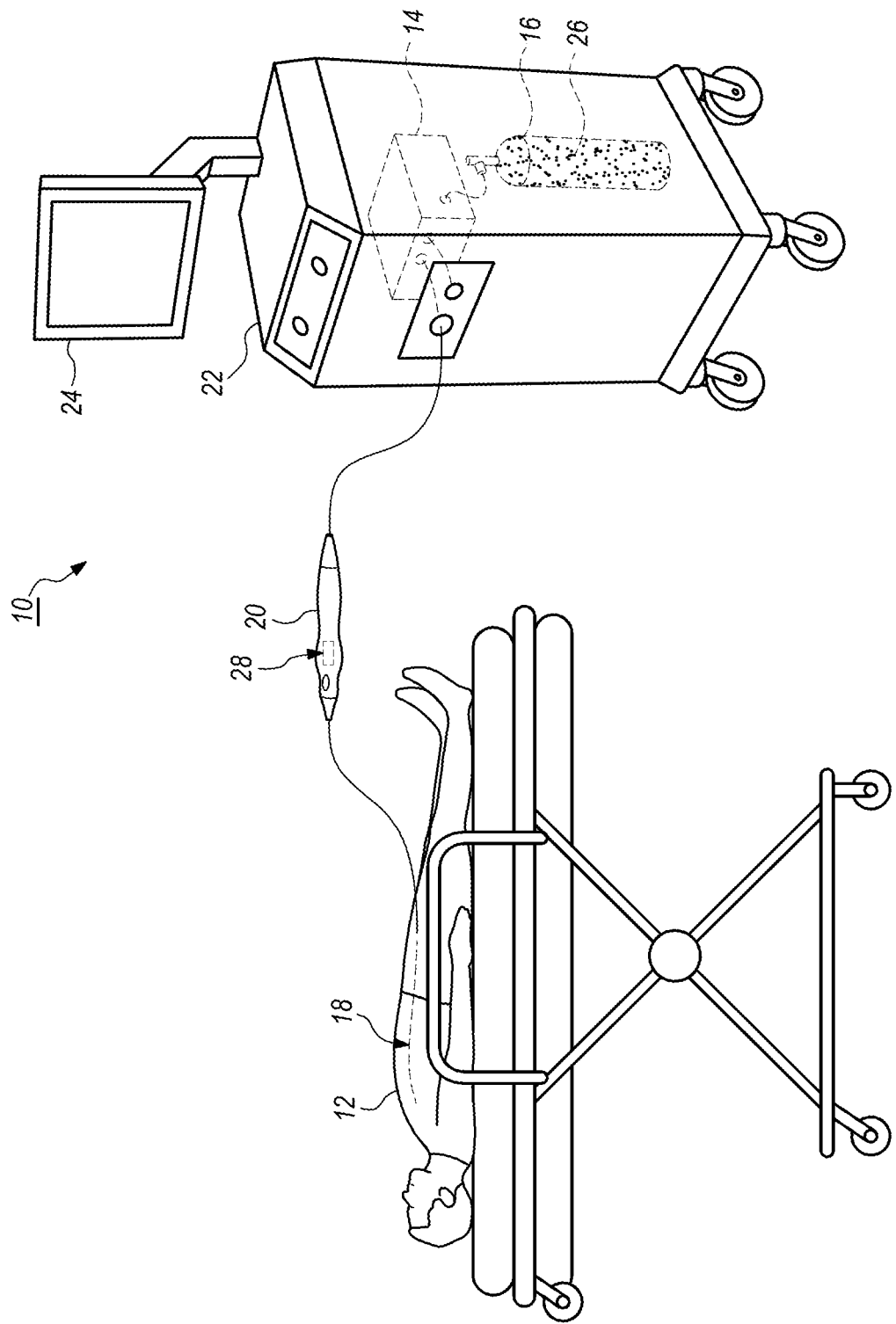
FIG. 1 is a simplified schematic side view illustration of a patient and an embodiment of an intravascular catheter system having features of the present invention, the intravascular catheter system including a balloon catheter, a handle assembly, and a fluid injection line compensation assembly.

FIG. 1 is a simplified schematic side view illustration of an embodiment of a medical device 10 for use with a patient 12, which can be a human being or an animal. Although the specific medical device 10 illustrated and described herein pertains to and refers to an intravascular catheter system 10 such as a cryogenic balloon catheter system, it is understood and appreciated that other types of medical devices 10 or systems can equally benefit by the teachings provided herein. For example, in certain non-exclusive alternative embodiments, the present invention can be equally applicable for use with any suitable types of ablation systems and/or any suitable types of catheter systems. Thus, the specific reference herein to use as part of an intravascular catheter system is not intended to be limiting in any manner.

The design of the intravascular catheter system 10 can be varied. In certain embodiments, such as the embodiment illustrated in FIG. 1, the intravascular catheter system 10 can include one or more of a control system 14 (illustrated in phantom), a fluid source 16 (illustrated in phantom), a balloon catheter 18, a handle assembly 20, a control console 22, a graphical display 24, and a fluid injection line compensation assembly 28 (also sometimes referred to herein simply as a "compensation assembly").

It is understood that although FIG. 1 illustrates the structures of the intravascular catheter system 10 in a particular position, sequence and/or order, these structures can be located in any suitably different position, sequence and/or order than that illustrated in FIG. 1. It is also understood that the intravascular catheter system 10 can include fewer or additional components than those specifically illustrated and described herein.

In various embodiments, the control system 14 is configured to monitor and control various processes of the ablation procedure. More specifically, the control system 14 can monitor and control release and/or retrieval of a cooling fluid 26 (e.g., a cryogenic fluid) to and/or from the balloon catheter 18. The control system 14 can also control various structures that are responsible for maintaining and/or adjusting a flow rate and/or pressure of the cryogenic fluid 26 that is released to the balloon catheter 18 during the cryoablation procedure. In such embodiments, the intravascular catheter system 10 delivers ablative energy in the form of cryogenic fluid 26 to cardiac tissue of the patient 12 to create tissue necrosis, rendering the ablated tissue incapable of conducting electrical signals. Additionally, in various embodiments, the control system 14 can control activation and/or deactivation of one or more other processes of the balloon catheter 18. Further, or in the alternative, the control system 14 can receive data and/or other information (hereinafter sometimes referred to as "sensor output") from various structures within the intravascular catheter system 10. In some embodiments, the control system 14 can receive, monitor, assimilate and/or integrate the sensor output, and/or any other data or information received from any structure within the intravascular catheter system 10 in order to control the operation of the balloon catheter 18. As provided herein, in various embodiments, the control system 14 can initiate and/or terminate the flow of cryogenic fluid 26 to the balloon catheter 18 based on the sensor output. Still further, or in the alternative, the control system 14 can control positioning of portions of the balloon catheter 18 within the body of the patient 12, and/or can control any other suitable functions of the balloon catheter 18.

The fluid source 16 contains the cryogenic fluid 26, which is delivered to the balloon catheter 18 with or without input from the control system 14 during a cryoablation procedure. Once the ablation procedure has initiated, the cryogenic fluid 26 can be delivered to the balloon catheter 18 and the resulting gas, after a phase change, can be retrieved from the balloon catheter 18, and can either be vented or otherwise discarded as exhaust. Additionally, the type of cryogenic fluid 26 that is used during the cryoablation procedure can vary. In one non-exclusive embodiment, the cryogenic fluid 26 can include liquid nitrous oxide. However, any other suitable cryogenic fluid 26 can be used. For example, in one non-exclusive alternative embodiment, the cryogenic fluid 26 can include liquid nitrogen.

The design of the balloon catheter 18 can be varied to suit the specific design requirements of the intravascular catheter system 10. As shown, the balloon catheter 18 is configured to be inserted into the body of the patient 12 during the cryoablation procedure, i.e. during use of the intravascular catheter system 10. In one embodiment, the balloon catheter 18 can be positioned within the body of the patient 12 using the control system 14. Stated in another manner, the control system 14 can control positioning of the balloon catheter 18 within the body of the patient 12. Alternatively, the balloon catheter 18 can be manually positioned within the body of the patient 12 by a healthcare professional (also referred to herein as an "operator"). As used herein, a healthcare professional and/or an operator can include a physician, a physician's assistant, a nurse and/or any other suitable person and/or individual. In certain embodiments, the balloon catheter 18 is positioned within the body of the patient 12 utilizing at least a portion of the sensor output that is received by the control system 14. For example, in various embodiments, the sensor output is received by the control system 14, which can then provide the operator with information regarding the positioning of the balloon catheter 18. Based at least partially on the sensor output feedback received by the control system 14, the operator can adjust the positioning of the balloon catheter 18 within the body of the patient 12 to ensure that the balloon catheter 18 is properly positioned relative to targeted cardiac tissue (not shown). While specific reference is made herein to the balloon catheter 18, as noted above, it is understood that any suitable type of medical device and/or catheter may be used.

The handle assembly 20 is handled and used by the operator to operate, position and control the balloon catheter 18. The design and specific features of the handle assembly 20 can vary to suit the design requirements of the intravascular catheter system 10. In the embodiment illustrated in FIG. 1, the handle assembly 20 is separate from, but in electrical and/or fluid communication with the control system 14, the fluid source 16 and/or the graphical display 24. In some embodiments, the handle assembly 20 can integrate and/or include at least a portion of the control system 14 within an interior of the handle assembly 20. It is understood that the handle assembly 20 can include fewer or additional components than those specifically illustrated and described herein.

In various embodiments, the handle assembly 20 can be used by the operator to initiate and/or terminate the cryoablation process, e.g., to start the flow of the cryogenic fluid 26 to the balloon catheter 18 in order to ablate certain targeted heart tissue of the patient 12. In certain embodiments, the control system 14 can override use of the handle assembly 20 by the operator. Stated in another manner, in some embodiments, based at least in part on the sensor output, the control system 14 can terminate the cryoablation process without the operator using the handle assembly 20 to do so.

The control console 22 is coupled to the balloon catheter 18 and the handle assembly 20. Additionally, in the embodiment illustrated in FIG. 1, the control console 22 includes at least a portion of the control system 14, the fluid source 16, and the graphical display 24. However, in alternative embodiments, the control console 22 can contain additional structures not shown or described herein. Still alternatively, the control console 22 may not include various structures that are illustrated within the control console 22 in FIG. 1. For example, in certain non-exclusive alternative embodiments, the control console 22 does not include the graphical display 24.

The graphical display 24 provides the operator of the intravascular catheter system 10 with information that can be used before, during and after the cryoablation procedure. For example, the graphical display 24 can provide the operator with information based on the sensor output, the timing output, and any other relevant information that can be used before, during and after the cryoablation procedure. The specifics of the graphical display 24 can vary depending upon the design requirements of the intravascular catheter system 10, or the specific needs, specifications and/or desires of the operator.

In one embodiment, the graphical display 24 can provide static visual data and/or information to the operator. In addition, or in the alternative, the graphical display 24 can provide dynamic visual data and/or information to the operator, such as video data or any other data that changes over time, e.g., during an ablation procedure. Further, in various embodiments, the graphical display 24 can include one or more colors, different sizes, varying brightness, etc., that may act as alerts to the operator. Additionally, or in the alternative, the graphical display 24 can provide audio data or information to the operator.

As provided herein, the compensation assembly 28 is configured to deliver the cryogenic fluid 26 from the fluid source 16 to the balloon catheter 18. Additionally, as noted above, the compensation assembly 28 is configured to compensate for necessary changes in length and/or positioning of a guidewire lumen 234 (illustrated in FIG. 2) during operation of the intravascular catheter system 10.

As illustrated, in various embodiments, at least a portion of the compensation assembly 28 can be positioned within the handle assembly 20. Additionally, or in the alternative, portions of the compensation assembly 28 can be positioned within other components of the intravascular catheter system 10, e.g., within the balloon catheter 18. The design and functioning of the components of various embodiments of the compensation assembly 28 are illustrated and described in greater detail herein below.

Figure 2:
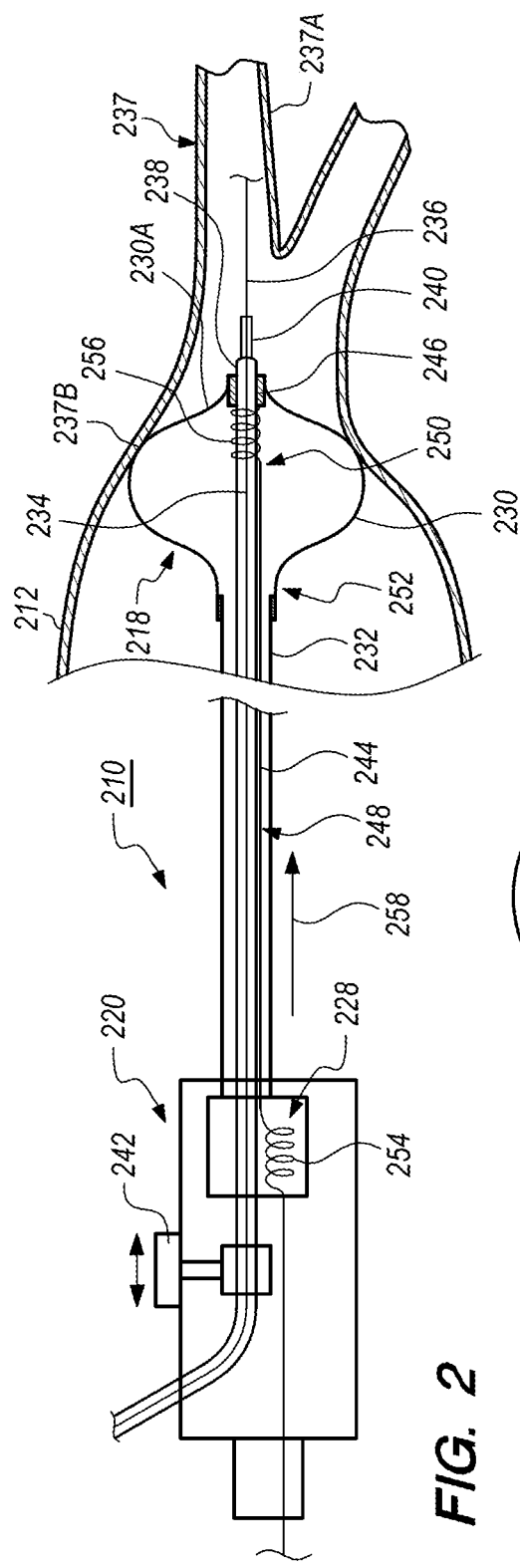
FIG. 2 is a simplified schematic side view illustration of a portion of the patient, and a portion of one embodiment of the intravascular catheter system including the balloon catheter and an embodiment of the fluid injection line compensation assembly.

FIG. 2 is a simplified schematic side view illustration of a portion of one embodiment of the intravascular catheter system 210 and a portion of a patient 212. In the embodiment illustrated in FIG. 2, the intravascular catheter system 210 includes one or more of the balloon catheter 218, the handle assembly 220, and the fluid injection line compensation assembly 228.

The balloon catheter 218 is inserted into the body of the patient 212 during the cryoablation procedure. The design of the balloon catheter 218 can be varied to suit the design requirements of the intravascular catheter system 210. In the embodiment illustrated in FIG. 2, the balloon catheter 218 includes one or more cryoballoons 230 (only one cryoballoon 230 is illustrated in FIG. 2 although greater than one cryoballoon 230 can be used), a catheter shaft 232, a guidewire lumen 234 and a guidewire 236. Alternatively, it is understood that the balloon catheter 218 can include other structures as well. However, for the sake of clarity, these other structures have been omitted from the Figures.

As shown in the embodiment illustrated in FIG. 2, the balloon catheter 218 is configured to be positioned within the circulatory system 237 of the patient 212. The guidewire 236 and guidewire lumen 234 are inserted into a pulmonary vein 237A of the patient 212, and the catheter shaft 232 and the cryoballoon 230 are moved along the guidewire 236 and/or the guidewire lumen 234 to near an ostium 237B of the pulmonary vein 237A. In general, it is the object of the balloon catheter 218 to seal the pulmonary vein 237A so that blood flow is occluded. Only when occlusion is achieved does the cryothermic energy, e.g., of the cryogenic fluid 26 (illustrated in FIG. 1), cause tissue necrosis which, in turn, provides for electrically blocking aberrant electrical signals (i.e. electrical isolation) that could otherwise trigger atrial fibrillation.

In various embodiments, the cryoballoon 230 can be secured, e.g., bonded, to the catheter shaft 232 and the guidewire lumen 234, which is distal to the catheter shaft 232. In the illustrated embodiment, for example, the cryoballoon 230 has a first end portion secured to a distal end of the shaft, and a second end portion attached to the guidewire lumen distal to the distal end of the shaft. Alternatively, the cryoballoon 230 can be secured to other suitable structures. It is appreciated that a variety of bonding techniques can be used and include heat-bonding and adhesive-bonding.

During use, upon sufficient inflation of the cryoballoon 230, an outer surface 230A of the cryoballoon 230 can be positioned within the circulatory system 237 of the patient 212 to abut and/or substantially form a seal with the ostium 237B of the pulmonary vein 237A to be treated. In particular, during use, it is generally desired that an outer diameter of the cryoballoon 230 be slightly larger than a diameter of the pulmonary vein 237A being treated to best enable occlusion of the pulmonary vein 237A. Having a cryoballoon 230 with an outer diameter that is either too small or too large can create problems that inhibit the ability to achieve the desired occlusion of the pulmonary vein 237A.

The specific design of and materials used for the cryoballoon 230 can be varied. For example, in various embodiments, specialty polymers with engineered properties can be used for forming the cryoballoon 230. In particular, some representative materials suitable for the cryoballoon 230 include various grades of polyether block amides (PEBA) such as the commercially available PEBAX® (marketed by Arkema, Colombes, France), or a polyurethane such as Pellathane™ (marketed by Lubrizol). Additionally, or in the alternative, the materials can include PET (polyethylene terephthalate), nylon, polyurethane, and other co-polymers of these materials, as non-exclusive examples. Further, the materials may be mixed in varying amounts to fine tune properties of the cryoballoon 230.

As illustrated, the guidewire lumen 234 encircles at least a portion of the guidewire 236. The design of the guidewire lumen 234 can vary. In some embodiments, the guidewire lumen 234 can include a guidewire lumen distal region 238 (also sometimes referred to herein as a "distal region"). The guidewire lumen distal region 238 includes a portion of the guidewire lumen 234 that is distal to the location where the cryoballoon 230 is secured to the guidewire lumen 234. The guidewire lumen distal region 238 can further include a distal tip 240. During use, the guidewire 236 is inserted into the guidewire lumen 234 and can course through the guidewire lumen 234 and extend out of the distal tip 240 of the guidewire lumen 234. In various embodiments, the guidewire 236 can also include a mapping catheter (not shown) that maps electrocardiograms in the heart, and/or can provide information needed to position at least portions of the balloon catheter 218 within the patient 212.

The handle assembly 220 is handled and used by the operator to operate, position and control the balloon catheter 218. The design of the handle assembly 220 can vary to suit the design requirements of the intravascular catheter system 210. In the embodiment illustrated in FIG. 2, the handle assembly 220 can include at least portions of one or more of the guidewire lumen 234, the guidewire 236, a guidewire lumen mover 242 and the compensation assembly 228, as described in greater detail herein.

The guidewire lumen mover 242 moves the guidewire lumen 234 during use of the intravascular catheter system 210. The operator can manually move the guidewire lumen mover 242 to extend or retract the guidewire lumen 234, before, during or after injection of the cryogenic fluid 26 into the cryoballoon 230. By moving the guidewire lumen mover 242 in a direction away from the cryoballoon 230, the guidewire lumen 234 is thereby retracted, and inflation of the cryoballoon 230 can then occur. Conversely, by moving the guidewire lumen mover 242 toward the cryoballoon 230, the guidewire lumen 234 is thereby extended, causing the cryoballoon 230 to collapse, perhaps in preparation for removal of the balloon catheter 218 from the patient 212, for example.

The fluid injection line compensation assembly 228 delivers cryogenic fluid 26 originating from the fluid source 16 (illustrated in FIG. 1) to the interior of the cryoballoon 230. The design of the compensation assembly 228 can be varied. In the embodiment illustrated in FIG. 2, the compensation assembly 228 includes a fluid injection line 244 and a fluid injection line stop 246. Additionally, as provided herein, the compensation assembly 228 compensates for necessary changes in length and/or positioning of the guidewire lumen 234 during operation of the intravascular catheter system 210 such that the fluid injection line 244 is extended and retracted in concert with the extension and retraction of the guidewire lumen 234.

The fluid injection line 244 is a tubular structure that acts as a conduit for the cryogenic fluid 26 that originates from the fluid source 16, and transports the cryogenic fluid 26 at least between the handle assembly 220 and the cryoballoon 230. The design, including the materials, size and shape of the fluid injection line 244 can vary. In one embodiment, the fluid injection line 244 can be formed at least partially from nitinol. Alternatively, other types of materials can be used or combined with nitinol. The fluid injection line 244 can extend at least from the handle assembly 220 to the cryoballoon 230, and can be at least partially positioned along and/or about the guidewire lumen 234.

In the embodiments shown and described herein, the fluid injection line 244 can include a proximal region 248 and a distal region 250. At least a portion of the proximal region 248 can be positioned within the handle assembly 220. Further, the proximal region 248 of the fluid injection line 244, as defined herein, extends from the handle assembly 220, along or near the guidewire lumen 234 to a point of entry 252 of the cryoballoon 230. Stated another way, the proximal region 248 is the portion of the fluid injection line 244 that is proximal (toward the handle assembly 220) to the cryoballoon 230. Conversely, the distal region 250 is the portion of the fluid injection line 244 positioned within the cryoballoon 230.

In the embodiment illustrated in FIG. 2, the fluid injection line 244 can include a compression spring 254 and a fluid discharge region 256. In one embodiment, the entire fluid injection line 244 is formed as a unitary structure. Alternatively, the fluid injection line 244 can be formed from two or more separate components that are secured together.

The compression spring 254 consistently exerts a bias force on the fluid discharge region 256 in a direction (as shown by arrow 258) away from the compression spring 254 and/or the handle assembly 220, and toward the distal tip 240 of the guidewire lumen distal region 238. The design of the compression spring 254 can be varied to suit the particular requirements of the compensation assembly 228. In one embodiment, the compression spring 254 is positioned within the handle assembly 220, at a location that is away from the cryoballoon 230. More specifically, in such embodiment, the proximal region 248 of the fluid injection line 244 can be configured to form the compression spring 254 that biases the distal region 250 in a direction 258 away from the proximal region 248. Alternatively, the compression spring 254 can be positioned outside of the handle assembly 220. Further, the force imparted by the compression spring 254 can vary depending upon the force required to maintain the necessary positioning of the fluid discharge region 256 relative to the cryoballoon 230 and/or the fluid injection line stop 246. The compression spring 254 can include any suitable configuration that generates a bias force on the fluid discharge region 256 against the fluid injection line stop 246.

The fluid discharge region 256 is a portion of the fluid injection line 244 that discharges the cryogenic fluid 26 into the cryoballoon 230. In some embodiments, as shown, the fluid discharge region 256 can include a coiled, tubular structure, and thus may sometimes be referred to as a "fluid line coil". As provided herein, the fluid discharge region 256 can include one or more fluid ports 360 (illustrated in FIG. 3, for example) through which the cryogenic fluid 26 exits the fluid injection line 244. The fluid discharge region 256 is positioned within the cryoballoon 230 and is maintained in such position due to the force imparted upon the fluid discharge region 256 by the compression spring 254. As described in greater detail below, the compression spring 254 and the fluid injection line stop 246 act in concert to maintain the positioning of the fluid discharge region 256 whether or not the cryoballoon 230 is in the inflated state or the deflated state, or whether or not the guidewire lumen 234 is being articulated or otherwise moved or positioned.

It is recognized that although the description and drawings provided herein focus on the fluid discharge region 256 being in the form of a coiled, tubular structure, the fluid discharge region 256 can likewise take on another suitable form. As one non-exclusive alternative example, the fluid discharge region 256 can take on the form of a plenum-like or manifold-type structure, or any other suitable structure, into which the fluid injection line 244 extends. In such embodiments, the fluid discharge region 356 can sometimes be referred to as a "fluid line plenum" or a "fluid line manifold". Additionally, in such embodiments, the fluid line plenum or fluid line manifold can include one or more fluid ports through which the cryogenic fluid 26 exits. Alternatively, the fluid discharge region 256 can have any other suitable configuration that may or may not coil around the guidewire lumen 234.

The fluid injection line stop 246 remains stationary relative to the guidewire lumen 234 and/or at least a portion of the cryoballoon 230, regardless of whether the cryoballoon 230 is in an inflated state, a partially deflated state or a completely deflated and/or extended state. The fluid injection line stop 246 can be formed from a relatively rigid material such as various metals, plastics, composite materials, or any other suitably rigid material(s). In one embodiment, the fluid injection line stop 246 can be secured directly to and/or can encircle a portion of the guidewire lumen 234. Alternatively, the fluid injection line stop 246 can be secured directly to a portion of the cryoballoon 230. The size of the fluid injection line stop 246 can vary. However, it is appreciated that the fluid injection line stop 246 should be of a sufficient size and/or shape to completely impede movement of the fluid injection line 244 more distal than the fluid injection line stop 246.

Further, it is understood that the fluid injection line stop 246 can be formed in various ways. As non-exclusive alternative examples, the fluid injection line stop 246 can be formed from (i) a distal segment of the cryoballoon 230 where the cryoballoon 230 is bonded to the guidewire lumen 234; (ii) a discrete cylindrical (or other shape) member of sufficient thickness to inhibit movement of the fluid discharge region 256 of the fluid injection line 244; (iii) an adhesive or another polymer that is appropriately positioned and has sufficient thickness to inhibit movement of the fluid discharge region 256 of the fluid injection line 244; or (iv) a stepped or raised section of the guidewire lumen 244 having a larger thickness or diameter than the remainder of the guidewire lumen 244. Still alternatively, any other suitable structure can form the fluid injection line stop 246.

With the designs provided herein, the compensation assembly 228 allows for extension and retraction of the fluid injection line 244 in concert with the moveable guidewire lumen 234, and can be integrated onto the guidewire lumen 234, thereby eliminating the need for a separate housing and means to separate the guidewire lumen 234 from the fluid injection line 244. Additionally, utilizing an immovably non-fixed fluid injection line 244 in conjunction with the fluid injection line stop 246 decreases or eliminates any moment acting on the guidewire lumen 234, thus reducing the tendency for bowing that can malposition the ports 360 in the fluid injection line 244.

Figure 3:
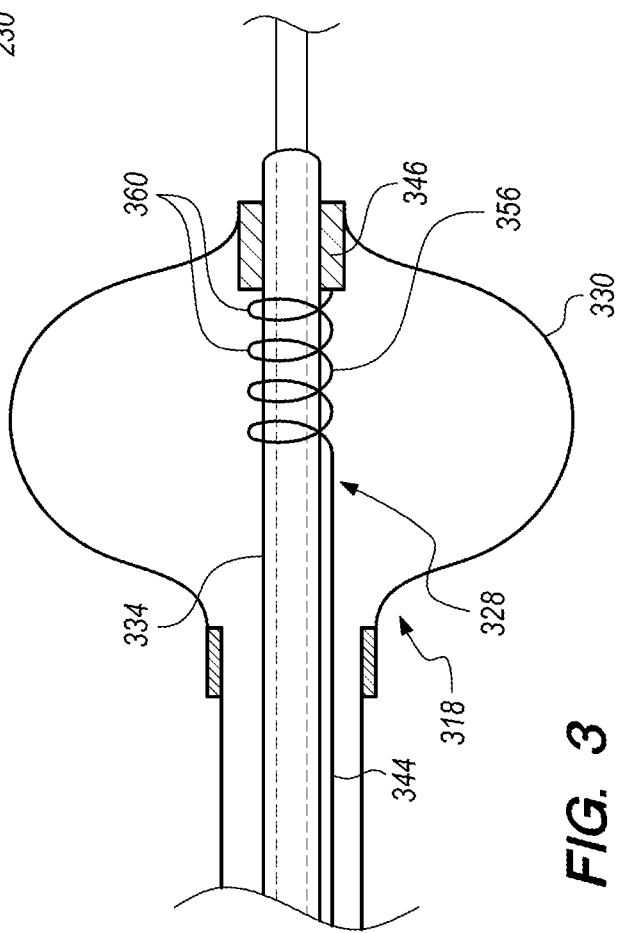
FIG. 3 is a simplified schematic side view illustration of a portion of one embodiment of the balloon catheter illustrated in an inflated state, and a portion of an embodiment of the fluid injection line compensation assembly.

FIG. 3 is a simplified schematic side view illustration of a portion of one embodiment of the balloon catheter 318 illustrated in an inflated state, and a portion of an embodiment of the fluid injection line compensation assembly 328. As noted, in FIG. 3, the cryoballoon 330 of the balloon catheter 318 is illustrated after having been inflated. Further, the guidewire lumen 334 has been retracted in a direction toward the handle assembly 220 (illustrated in FIG. 2). It is appreciated that, in various embodiments, the retracted state or position of the guidewire lumen 334 allows for and/or substantially coincides with the inflation of the cryoballoon 330.

Additionally, as shown in this embodiment, the fluid discharge region 356 of the fluid injection line 344 is positioned against the fluid injection line stop 346. As provided previously herein, the compression spring 254

(illustrated in FIG. 2) has imparted a force on the fluid discharge region 356 in a direction toward the fluid injection line stop 346 such that the fluid discharge region 356 can be effectively maintained in position against the fluid injection line stop 346. In the position illustrated in FIG. 3, the fluid ports 360 are suitably positioned to emit cryogenic fluid 26 (illustrated in FIG. 1) that has been delivered from the fluid source 16 (illustrated in FIG. 1) through the fluid injection line 344 to the desired location(s) on the cryoballoon 330. Further, as shown, the portion of the fluid discharge region 356 that includes the fluid ports 360 can have a substantially coiled structure, which can be coiled about and/or adjacent to the guidewire lumen 334. As noted above, the coiled structure of the fluid discharge region 356 of the fluid injection line 344 that includes the fluid ports 360 can also be referred to as a "fluid line coil". Thus, in such embodiments, the fluid ports 360 can be said to be positioned on the fluid line coil.

FIG. 4 is a simplified schematic side view illustration of a portion of one embodiment of the balloon catheter 418 illustrated in a deflated state, and a portion of an embodiment of the fluid injection line compensation assembly 428. As noted, in FIG. 4, the cryoballoon 430 is illustrated after having been deflated. Further, the guidewire lumen 434 has been at least partially extended in a direction away from the handle assembly 220 (illustrated in FIG. 2).

Additionally, as shown in this embodiment, the fluid discharge region 456 of the fluid injection line 444 is maintained against the fluid injection line stop 446. As provided previously herein, the compression spring 254 (illustrated in FIG. 2) has imparted a force on the fluid discharge region 456 in a direction toward the fluid injection line stop 446 such that the fluid discharge region 456 can be effectively maintained in position against the fluid injection line stop 446.

FIG. 5 is a simplified schematic side view illustration of a portion of one embodiment of the balloon catheter 518 illustrated in an extended state, and a portion of an embodiment of the fluid injection line compensation assembly 528. In particular, in FIG. 5, the cryoballoon 530 is illustrated after having been fully deflated and extended. Further, the guidewire lumen 534 has been substantially fully extended in a direction away from the handle assembly 220 (illustrated in FIG. 2). It is appreciated that, in various embodiments, the extended state or position of the guidewire lumen 534 allows for and/or substantially coincides with the deflation of the cryoballoon 530.

Additionally, as shown in this embodiment, the fluid discharge region 556 of the fluid injection line 544 is again maintained against the fluid injection line stop 546. As provided previously herein, the compression spring 254 (illustrated in FIG. 2) has imparted a force on the fluid discharge region 556 in a direction toward the fluid injection line stop 346 such that the fluid discharge region 556 can be effectively maintained in position against the fluid injection line stop 546.

Figure 6:
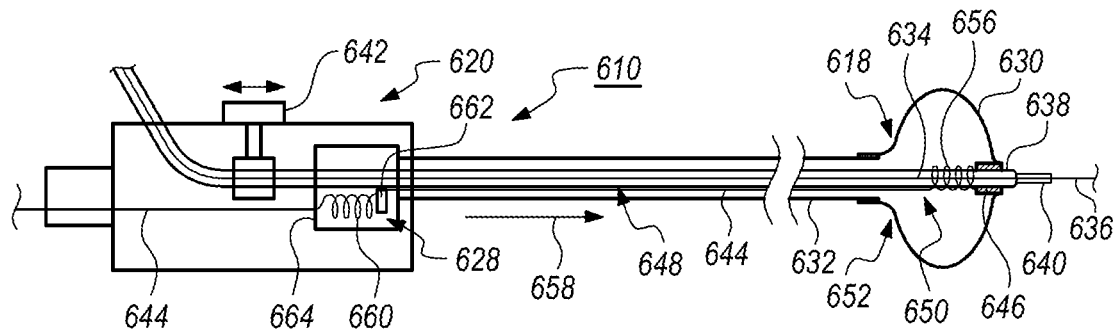
FIG. 6 is a simplified schematic side view illustration of a portion of another embodiment of the intravascular catheter system, including the balloon catheter and another embodiment of the fluid injection line compensation assembly.

FIG. 6 is a simplified schematic side view illustration of a portion of another embodiment of the intravascular catheter system 610. In this embodiment, the intravascular catheter system 610 includes a balloon catheter 618, a handle assembly 620, and another embodiment of the fluid injection line compensation assembly 628.

As illustrated and described herein, the balloon catheter 618 is substantially similar to what has been illustrated and described herein above. For example, the balloon catheter 618 is again configured to be inserted into the body of the patient 12 (illustrated in FIG. 1) during the cryoablation procedure. Additionally, in the embodiment illustrated in FIG. 6, the balloon catheter 618 again includes one or more cryoballoons 630 (only one cryoballoon 630 is illustrated in FIG. 6 although greater than one cryoballoon 630 can be used), a catheter shaft 632, a guidewire lumen 634 and a guidewire 636. Alternatively, the balloon catheter 618 can include additional components or fewer components than those specifically illustrated and described herein.

As above, in various embodiments, the cryoballoon 630 can be secured, e.g., bonded, to the catheter shaft 632 and the guidewire lumen 634, which is distal to the catheter shaft 632. It is appreciated that the cryoballoon 630 can be secured to the catheter shaft 632 and the guidewire lumen 634 in any suitable manner. Alternatively, the cryoballoon 630 can be secured to other suitable structures.

Additionally, as with the previous embodiment, the guidewire lumen 634 encircles at least a portion of the guidewire 636. In some embodiments, the guidewire lumen 634 can include a guidewire lumen distal region 638 (also sometimes referred to herein as a "distal region"). The guidewire lumen distal region 638 includes a portion of the guidewire lumen 634 that is distal to the location where the cryoballoon 630 is secured to the guidewire lumen 634. The guidewire lumen distal region 638 can further include a distal tip 640. During use, the guidewire 636 is inserted into the guidewire lumen 634 and can course through the guidewire lumen 634 and extend out of the distal tip 640 of the guidewire lumen 634. In various embodiments, the guidewire 636 can also include a mapping catheter (not shown) that maps electrocardiograms in the heart, and/or can provide information needed to position at least portions of the balloon catheter 618 within the patient 12.

Further, as with the previous embodiment, the handle assembly 620 is handled and used by the operator to operate, position and control the balloon catheter 618. In the embodiment illustrated in FIG. 6, the handle assembly 620 includes at least portions of one or more of the guidewire lumen 634, the guidewire 636, a guidewire lumen mover 642 and the fluid injection line compensation assembly 628. The guidewire lumen 634, the guidewire 636 and the guidewire lumen mover 642 can all operate in a somewhat similar manner as those previously described herein.

As with the previous embodiment, the compensation assembly 628 is again used to deliver cryogenic fluid 26 (illustrated in FIG. 1) originating from the fluid source 16 (illustrated in FIG. 1) to the interior of the cryoballoon 630. Further, the compensation assembly 628 again compensates for necessary changes in length and/or positioning of the guidewire lumen 634 during operation of the intravascular catheter system 610.

However, in this embodiment, the compensation assembly 628 has a somewhat different design than the previous embodiment. In particular, in the embodiment illustrated in FIG. 6, the compensation assembly 628 includes a fluid injection line 644, a fluid injection line stop 646, a fluid injection line bias 660, a distal bias stop 662 and a proximal bias stop 664.

As with the previous embodiment, the fluid injection line 644 is a tubular structure that acts as a conduit for the cryogenic fluid 26 that originates from the fluid source 16, and transports the cryogenic fluid 26 at least between the handle assembly 620 and the cryoballoon 630. The design, including the materials, size and shape of the fluid injection line 644 can vary. In one embodiment, the fluid injection line 644 can be formed at least partially from nitinol. Alternatively, other types of materials can be used or combined with nitinol. The fluid injection line 644 can extend at least from the handle assembly 620 to the cryoballoon 630, and can be at least partially positioned along and/or about the guidewire lumen 634.

Additionally, in this embodiment, the fluid injection line 644 again includes a proximal region 648 and a distal region 650. At least a portion of the proximal region 648 can be positioned within the handle assembly 620. Further, the proximal region 648 of the fluid injection line 644, as defined herein, extends from the handle assembly 620, along or near the guidewire lumen 634 to a point of entry 652 of the cryoballoon 630. Stated another way, the proximal region 648 is the portion of the fluid injection line 644 that is proximal (toward the handle assembly 620) to the cryoballoon 630. Conversely, the distal region 650 is the portion of the fluid injection line 644 positioned within the cryoballoon 630.

In the embodiment illustrated in FIG. 6, the fluid injection line 644 again includes a fluid discharge region 656. In one embodiment, the fluid discharge region 656 can be positioned and can operate in a somewhat similar manner, if not identically, to that previously described herein.

The fluid injection line stop 646 remains stationary relative to the guidewire lumen 634 and/or at least a portion of the cryoballoon 630, regardless of whether the cryoballoon 630 is in an inflated state, a partially deflated state or a completely deflated and/or extended state. In one embodiment, the fluid injection line stop 646 can be positioned and can operate in a somewhat similar manner, if not identically, to that previously described herein.

The fluid injection line bias 660 consistently exerts a bias force on the distal bias stop 662 in a direction (shown by arrow 658) from the handle assembly 620 toward the fluid injection line stop 646, e.g., toward the distal tip 640 of the guidewire lumen distal region 638. The form and/or design of the fluid injection line bias 660 can vary. In one embodiment, the fluid injection line bias 660 is a spring. In alternative embodiments, the fluid line injection bias 660 can be any other suitable type of biasing member. In the embodiment illustrated in FIG. 6, the fluid injection line bias 660 is positioned between the distal bias stop 662 and the proximal bias stop 664.

As shown in the embodiment illustrated in FIG. 6, the distal bias stop 662 can be directly or indirectly secured to the fluid injection line 644. Therefore, in this embodiment, the fluid injection line bias 660 biases not only the distal bias stop 662, but also simultaneously biases the fluid injection line 644 in the same direction 658. Thus, it is appreciated that in this embodiment, the distal bias stop 662 is movable within the handle assembly 620.

The proximal bias stop 664 is positioned more proximally than the distal bias stop 662, so that the distal bias stop 662 is positioned between the proximal bias stop 664 and the cryoballoon 630. The proximal bias stop 664 is substantially stationary within the handle assembly 620.

With this design, the fluid injection line bias 660 imparts a force on the distal bias stop 662 that causes the fluid injection line 644 and/or the fluid discharge region 656 to be biased toward and/or against the fluid injection line stop 646. This bias maintains the fluid discharge region 656 in a substantially consistent position and/or orientation relative to the cryoballoon 630 and/or the guidewire lumen 634 in the vicinity of the cryoballoon 630. Further, with the designs provided herein, the compensation assembly 628 allows for extension and retraction of the fluid injection line 644 in concert with the moveable guidewire lumen 634. Additionally, utilizing an immovably non-affixed fluid injection line 644 in conjunction with the fluid injection line stop 646 decreases or eliminates any moment acting on the guidewire lumen 634, thus reducing the tendency for bowing that can malposition the ports 360 (illustrated in FIG. 3) in the fluid injection line 644.

Figure 7A:
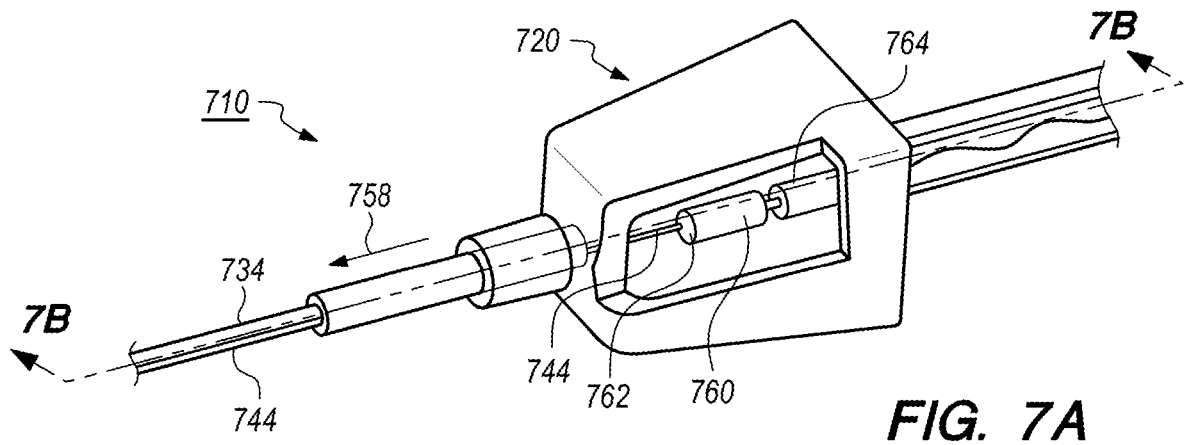
FIG. 7A is a simplified schematic perspective view illustration of a portion of still another embodiment of the intravascular catheter system, including a portion of the handle assembly and a portion of still another embodiment of the fluid injection line compensation assembly.

FIG. 7A is a simplified schematic perspective view illustration of a portion of an embodiment of the intravascular catheter system 710, including a portion of the handle assembly 720 and a portion of an embodiment of the fluid injection line compensation assembly 728. In this embodiment, the compensation assembly 728 can operate in a somewhat similar manner as that previously described with respect to FIG. 6. Additionally, the compensation assembly 728 again compensates for necessary changes in length and/or positioning of the guidewire lumen 734 during operation of the intravascular catheter system 710.

In the embodiment illustrated in FIG. 7A, the compensation assembly 728 includes a fluid injection line 744, a fluid injection line bias 760, a distal bias stop 762 and a proximal bias stop 764.

The fluid injection line bias 760 can consistently exert a bias force on the distal bias stop 762 in a direction 758 toward the fluid injection line stop 646 (illustrated in FIG. 6). The form and/or design of the fluid injection line bias 760 can vary. In one embodiment, the fluid injection line bias 760 is a spring. In alternative embodiments, the fluid line injection bias 760 can be any other suitable type of biasing member. In the embodiment illustrated in FIG. 7A, the fluid injection line bias 760 is positioned between the distal bias stop 762 and the proximal bias stop 764.

Additionally, as shown in the embodiment illustrated in FIG. 7A, the distal bias stop 762 can be directly or indirectly secured to the fluid injection line 744. Therefore, in this embodiment, the fluid injection line bias 760 biases not only the distal bias stop 762, but also simultaneously biases the fluid injection line 744 in the same direction 758. Thus, it is appreciated that in this embodiment, the distal bias stop 762 is movable within the handle assembly 720.

The proximal bias stop 764 is positioned more proximally than the distal bias stop 762, so that the distal bias stop 762 is positioned between the proximal bias stop 764 and the cryoballoon 630 (illustrated in FIG. 6). The proximal bias stop 764 is substantially stationary within the handle assembly 720.

Figure 7B:
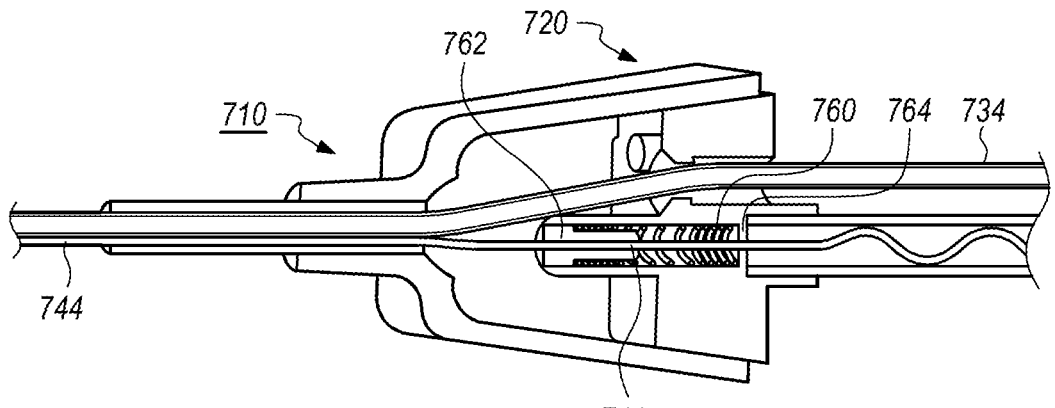
FIG. 7B is a simplified schematic cross-sectional view illustration of the portion of the intravascular catheter system taken on line 7B-7B in FIG. 7A.

FIG. 7B is a cross-sectional view of the portion of the embodiment of the intravascular catheter system 710 taken on line 7B-7B in FIG. 7A. In particular, FIG. 7B illustrates certain components of the intravascular catheter system 710 in greater detail. In this embodiment, as shown in FIG. 7B, the fluid injection line bias 760 is positioned between the distal bias stop 762 and the proximal bias stop 764. Additionally, as noted above, the distal bias stop 762 is movable within the handle assembly 720. Further, the proximal bias stop 764 is positioned more proximally than the distal bias stop 762, so that the distal bias stop 762 is positioned between the proximal bias stop 764 and the cryoballoon 630 (illustrated in FIG. 6). In this embodiment, the proximal bias stop 764 is substantially stationary within the handle assembly 720.

FIG. 8A is a simplified schematic side view illustration of a portion of yet another embodiment of the intravascular catheter system 810, including the balloon catheter 818, the handle assembly 820, and yet another embodiment of the fluid injection line compensation assembly 828.

As illustrated and described herein, the balloon catheter 818 is substantially similar to what has been illustrated and described in the above embodiments. For example, the balloon catheter 818 is again configured to be inserted into the body of the patient 12 (illustrated in FIG. 1) during the cryoablation procedure. Additionally, in the embodiment illustrated in FIG. 8A, the balloon catheter 818 again includes one or more cryoballoons 830 (only one cryoballoon 830 is illustrated in FIG. 8A although greater than one cryoballoon 830 can be used), a catheter shaft 832, a guidewire lumen 834 and a guidewire 836. Alternatively, the balloon catheter 818 can include additional components or fewer components than those specifically illustrated and described herein.

As above, in various embodiments, the cryoballoon 830 can be secured, e.g., bonded, to the catheter shaft 632 and the guidewire lumen 834, which is distal to the catheter shaft 832. It is appreciated that the cryoballoon 830 can be secured to the catheter shaft 832 and the guidewire lumen 832 in any suitable manner. Alternatively, the cryoballoon 830 can be secured to other suitable structures.

Additionally, as with the previous embodiments, the guidewire lumen 834 encircles at least a portion of the guidewire 836. In some embodiments, the guidewire lumen 834 can include a guidewire lumen distal region 638 (also sometimes referred to herein as a "distal region"). The guidewire lumen distal region 838 includes a portion of the guidewire lumen 834 that is distal to the location where the cryoballoon 830 is secured to the guidewire lumen 834. The guidewire lumen distal region 838 can further include a distal tip 840. During use, the guidewire 836 is inserted into the guidewire lumen 834 and can course through the guidewire lumen 834 and extend out of the distal tip 840 of the guidewire lumen 834. In various embodiments, the guidewire 836 can also include a mapping catheter (not shown) that maps electrocardiograms in the heart, and/or can provide information needed to position at least portions of the balloon catheter 818 within the patient 12.

Further, as with the previous embodiments, the handle assembly 820 is handled and used by the operator to operate, position and control the balloon catheter 818. In the embodiment illustrated in FIG. 8A, the handle assembly 820 can include one or more of a handle manifold 821, and at least portions of the guidewire lumen 834, the guidewire 836, a guidewire lumen mover 842 and the fluid injection line compensation assembly 828, as described in greater detail herein. The handle manifold 821 can house portions of one or more of the guidewire lumen 834, the guidewire 836 and the fluid injection line compensation assembly 828. In one embodiment, the handle manifold 821 can also include one or more guidewire lumen sealers 867 (also sometimes referred to herein as "lumen sealers" or simply as "sealers").

The lumen sealer(s) 867 provides a seal around the guidewire lumen 834 within the handle assembly 820. Further, or in the alternative, the lumen sealer 867 can impart a frictional force upon the guidewire lumen 834 that is overcome by movement of the guidewire lumen mover 842 during either extension or retraction of the cryoballoon 830. In one embodiment, the lumen sealer 867 can include one or more O-rings (two O-rings are illustrated in FIG. 8A) through which the guidewire lumen 834 passes. However, another type of lumen sealer 867 can be used. As one non-exclusive example, the lumen sealer 867 can include an electronic actuator that exerts a frictional force on the guidewire lumen 834. Alternatively, the lumen sealer 867 can include a solenoid, a set screw, or any other suitable manner of generating a certain frictional force to selectively maintain the positioning of the guidewire lumen 834. In one embodiment, the level of friction that is generated by the lumen sealer 867 can be tuned and/or varied as needed. In various embodiments, the lumen sealer 867 does not impart a bias force on the guidewire lumen 834 that causes movement of the guidewire lumen 834 in either the distal (extended) or proximal (retracted) direction.

The guidewire lumen 834, the guidewire 836 and the guidewire lumen mover 842 can all operate in a somewhat similar manner as those previously described herein.

As with the previous embodiments, the compensation assembly 828 is again used to deliver cryogenic fluid 26 (illustrated in FIG. 1) originating from the fluid source 16 (illustrated in FIG. 1) to the interior of the cryoballoon 830. Further, the compensation assembly 828 again compensates for necessary changes in length and/or positioning of the guidewire lumen 834 during operation of the intravascular catheter system 810.

However, the compensation assembly 828 illustrated in FIG. 8A has a somewhat different design than the previous embodiments. More specifically, in the embodiment illustrated in FIG. 8A, the compensation assembly 828 includes a fluid injection line 844, a distal fluid injection line stop 846D, a proximal fluid injection line stop 846P, and one or more injection line frictional elements 868 (also referred to herein simply as "frictional elements").

As with the previous embodiments, the fluid injection line 844 is a tubular structure that acts as a conduit for the cryogenic fluid 26 that originates from the fluid source 16, and transports the cryogenic fluid 26 at least between the handle assembly 820 and the cryoballoon 830. The design, including the materials, size, configuration and shape of the fluid injection line 844 can vary. In one embodiment, the fluid injection line 844 can be formed at least partially from nitinol. Alternatively, other types of materials can be used or combined with nitinol. The fluid injection line 844 can extend at least from the handle assembly 820 to the cryoballoon 830, and can be at least partially positioned along and/or about the guidewire lumen 834.

Additionally, in this embodiment, the fluid injection line 844 again includes a proximal region 848 and a distal region 850. At least a portion of the proximal region 848 can be positioned within the handle assembly 820. Further, the proximal region 848 of the fluid injection line 844, as defined herein, extends from the handle assembly 820, along or near the guidewire lumen 834 to a point of entry 852 of the cryoballoon 830. Stated another way, the proximal region 848 is the portion of the fluid injection line 844 that is proximal (toward the handle assembly 820) to the cryoballoon 830. Conversely, the distal region 850 is the portion of the fluid injection line 844 positioned within the cryoballoon 830.

In the embodiment illustrated in FIG. 8A, the fluid injection line 844 again includes a fluid discharge region 856. In one embodiment, the fluid discharge region 856 can be positioned and can operate in a somewhat similar manner, if not identically, to that previously described herein. However, in the embodiment illustrated in FIG. 8A, the fluid discharge region 856 is not affixed to the guidewire lumen 834. As a result, the fluid discharge region 856 is free to move both longitudinally along and/or rotationally about the guidewire lumen 834 if necessary.

As shown, the distal fluid injection line stop 846D is positioned further away from the handle assembly 820 than the proximal fluid injection line stop 846P. In one embodiment, the distal fluid injection line stop 846D can be secured to and can remain stationary relative to the guidewire lumen 834 and/or at least a portion of the cryoballoon 830, regardless of whether the cryoballoon 830 is in an inflated state, a partially deflated state or a completely deflated and/or extended state. Alternatively, the distal fluid injection line stop 846D can be secured to another structure of the balloon catheter 818. In one embodiment, the distal fluid injection line stop 846D can be positioned and can operate in a somewhat similar manner, if not identically, to that of the fluid injection line stops previously described herein.

The proximal fluid injection line stop 846P is positioned toward the handle assembly 820 from the distal fluid injection line stop 846D. In one embodiment, the proximal fluid injection line stop 846P can be secured to and can remain stationary relative to the guidewire lumen 834. Alternatively, the proximal fluid injection line stop 846P can be secured to another structure of the balloon catheter 818.

The distal and proximal fluid injection line stops 846D, 846P, are positioned along or near the guidewire lumen 834 so that the fluid discharge region 856 is positioned directly therebetween. In one embodiment, because the fluid discharge region 856 can be coiled (or otherwise positioned) around the guidewire lumen 834 and positioned between the distal and proximal fluid injection line stops 846D, 846P, the distal and proximal fluid injection line stops 846D, 846P form limitations of movement of the fluid discharge region 856 along the guidewire lumen 834. However, in the embodiment illustrated in FIG. 8A, no rotational movement limitations are present.

The frictional element(s) 868 imparts a frictional force upon the fluid injection line 844 that is overcome by movement of the guidewire lumen 834 during either extension or retraction of the cryoballoon 830. In one embodiment, the frictional element 868 can include one or more O-rings (two O-rings are illustrated in FIG. 8A) through which the fluid injection line 844 passes. However, other frictional elements 868 can be used. As one non-exclusive example, the frictional element 868 can include an electronic actuator that exerts a frictional force on the fluid injection line 844. Alternatively, the frictional element 868 can include a solenoid, a set screw, or any other suitable manner of generating friction to selectively maintain the positioning of the fluid injection line 844. In one embodiment, the level of friction that is generated by the frictional element 868 can be tuned and/or varied as needed. In various embodiments, the frictional element 868 maintains the positioning of the fluid injection line 844 absent movement by the guidewire lumen 834.

In operation, in one embodiment, when the guidewire lumen mover 842 is moved, causing the guidewire lumen 834 to move, the distal and proximal fluid injection line stops 846D, 846P move with the guidewire lumen 834. Movement of the distal and proximal fluid injection line stops 846D, 846P against the fluid discharge region 856 will move the fluid discharge region 856, and thus, the fluid injection line 844, in a distal and/or a proximal direction.

Additionally, in the embodiment illustrated in FIG. 8A, the balloon catheter 818 can include one or more couplers 870 that hold the fluid injection line 844 adjacent to the guidewire lumen 834. The couplers 870 can have any suitable design.

FIG. 8B is a cross-sectional view of a portion of the balloon catheter 818 taken on line 8B-8B in FIG. 8A. As shown in FIG. 8B, in this embodiment, the guidewire lumen 834, the guidewire 836 and the fluid injection line 844 are at least partially encircled by the coupler 870. Additionally, the coupler 870 can keep the fluid injection line 844 immediately adjacent to the guidewire lumen 834. In one embodiment, the coupler 870 inhibits relative movement between the fluid injection line 844 and the guidewire lumen 834 at the location of the coupler 870. Alternatively, the coupler 870 can permit slight or moderate movement between the fluid injection line 844 and the guidewire lumen 834 at the location of the coupler 870.

The number of couplers 870 along the guidewire lumen 834 and the fluid injection line 844 can vary as required by the intravascular catheter system 810 (illustrated in FIG. 8A). In one embodiment, the coupler 870 can be formed from any suitable material that can adequately hold the fluid injection line 844 to the guidewire lumen 834 without causing excessive deformation or pinching of these structures. In one non-exclusive embodiment, the coupler 870 can be formed from a relatively thin plastic material that can allow slight movement or no movement between the fluid injection line 844 and the guidewire lumen 834.

Figure 9A:
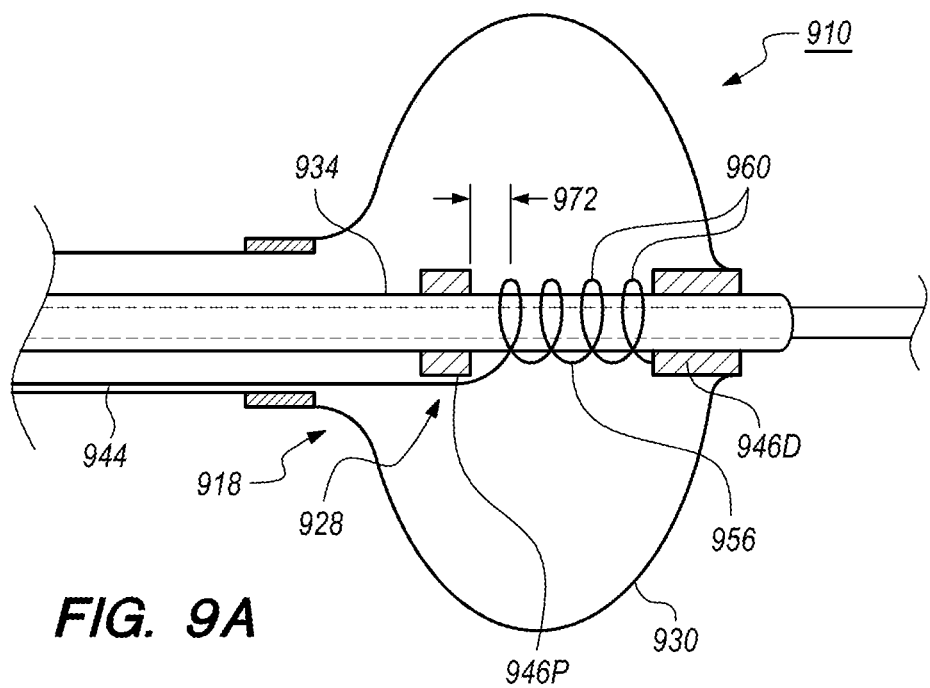
FIG. 9A is a simplified, schematic partial cross-sectional view illustration of a portion of another embodiment of the intravascular catheter system, including the balloon catheter illustrated in the inflated state, and a portion of another embodiment of the fluid injection line compensation assembly.

FIG. 9A is a simplified, schematic partial cross-sectional view illustration of a portion of another embodiment of the intravascular catheter system 910, including the balloon catheter 918 illustrated in the inflated state, and a portion of another embodiment of the fluid injection line compensation assembly 928. In the embodiment illustrated in FIG. 9A, the guidewire lumen 934 has been retracted in a direction toward the handle assembly 820 (illustrated in FIG. 8A).

Additionally, in this embodiment, the fluid discharge region 956 of the fluid injection line 944 is positioned between the distal fluid injection line stop 946D and the proximal fluid injection line stop 946P. As shown, the spacing between the distal fluid injection line stop 946D and the proximal fluid injection line stop 946P can be greater than a distance along the guidewire lumen 934 taken up by the fluid discharge region 956. Thus, in this embodiment, a gap 972 is present between the fluid discharge region 956 and at least one of the distal fluid injection line stop 946D and the proximal fluid injection line stop 946P. In embodiments wherein the fluid discharge region 956 is not affixed and/or bonded to the guidewire lumen 934, the gap 972 can thus allow for slight longitudinal and/or rotational movement of the fluid discharge region 956 relative to the guidewire lumen 934. In the position illustrated in FIG. 9A, the fluid ports 960 are suitably positioned to emit cryogenic fluid 26 (illustrated in FIG. 1) to the desired location(s) within the cryoballoon 930.

Figure 9B:
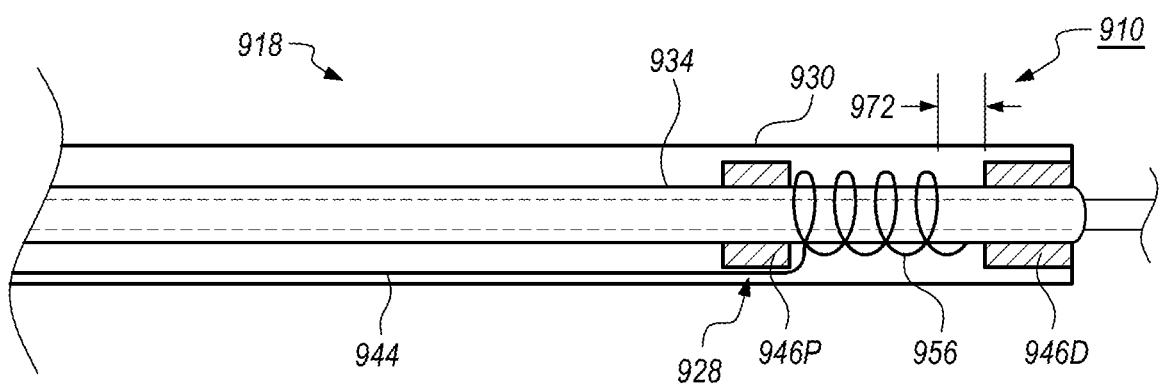
FIG. 9B is a simplified schematic side view illustration of the portion of the intravascular catheter system illustrated in FIG. 9A, including the balloon catheter illustrated in the deflated state.

FIG. 9B is a simplified schematic side view illustration of the portion of intravascular catheter system 910 illustrated in FIG. 9A, including the balloon catheter 918, shown in the deflated state. As shown, in the deflated (or extended) state, the fluid discharge region 956 is still positioned between the distal fluid injection line stop 946D and the proximal fluid injection line stop 946P of the compensation assembly 928. However, in one embodiment, the positioning of the gap 972 may have moved relative to the distal fluid injection line stop 946D and the proximal fluid injection line stop 946P because the fluid discharge region 956 is not affixed to the guidewire lumen 934. For example, in such embodiment, the gap 972 can move from being positioned adjacent to the proximal fluid injection line stop 946P when the balloon catheter 918 is in the inflated state (as shown in FIG. 9A) to being positioned adjacent to the distal fluid injection line stop 946D when the balloon catheter 918 is in the deflated state (as shown in FIG. 9B). Alternatively, the positioning of the gap 972 can remain substantially consistent whether the cryoballoon 930 is inflated (illustrated in FIG. 9A) or deflated.

With this design, the fluid injection line stops 946D, 946P on the guidewire lumen 934 allow for the fluid discharge region 956 to freely rotate, thereby reducing a moment arm on the fluid discharge region 956. Further, likelihood of torqueing the guidewire lumen 934 unnecessarily is reduced.

Figure 10A:
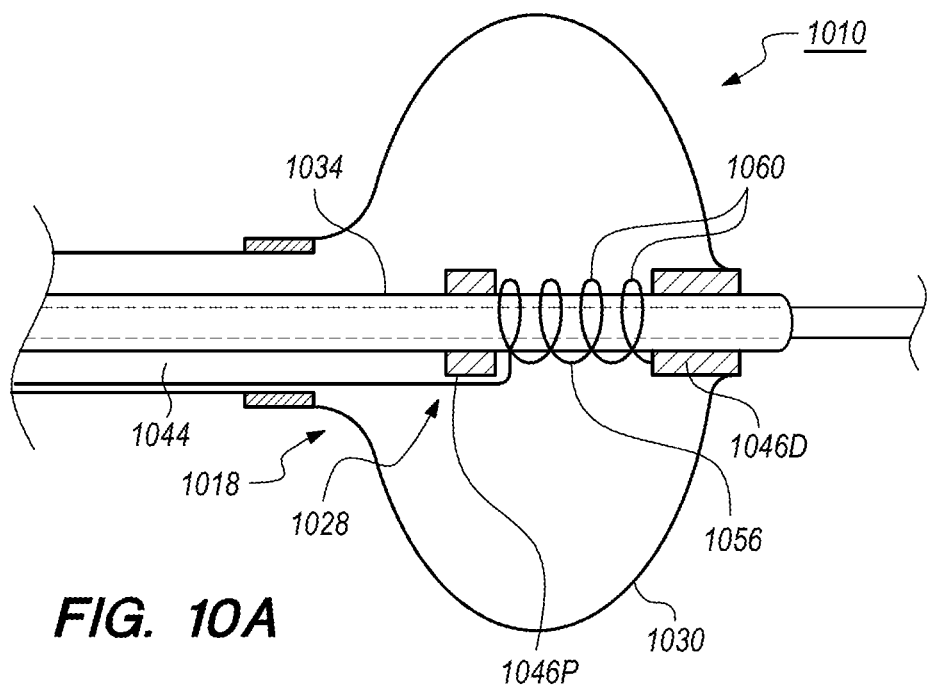
FIG. 10A is a simplified, schematic partial cross-sectional view illustration of a portion of still yet another embodiment of the intravascular catheter system, including the balloon catheter illustrated in the inflated state, and a portion of still yet another embodiment of the fluid injection line compensation assembly.

FIG. 10A is a simplified, schematic partial cross-sectional view of a portion of still yet another embodiment of the intravascular catheter system 1010, including the balloon catheter 1018 illustrated in the inflated state, and a portion of still yet another embodiment of the fluid injection line compensation assembly 1028. In the embodiment illustrated in FIG. 10A, the guidewire lumen 1034 has been retracted in a direction toward the handle assembly 820 (illustrated in FIG. 8A).

Additionally, in this embodiment, the fluid discharge region 1056 of the fluid injection line 1044 is positioned between the distal fluid injection line stop 1046D and the proximal fluid injection line stop 1046P. In this embodiment, the spacing between the distal fluid injection line stop 1046D and the proximal fluid injection line stop 1046P is approximately the same as a distance along the guidewire lumen 1034 taken up by the fluid discharge region 1056. Thus, in this embodiment, no gap 972 (illustrated in FIG. 9A) is present between the fluid discharge region 1056 and either of the distal fluid injection line stop 1046D or the proximal fluid injection line stop 1046P. However, in one embodiment, because the fluid discharge region 1056 is not affixed and/or bonded to the guidewire lumen 1034, slight rotational movement of the fluid discharge region 1056 relative to the guidewire lumen 1034 can still occur. In the position illustrated in FIG. 10A, the fluid ports 1060 are suitably positioned to emit cryogenic fluid 26 (illustrated in FIG. 1) to the desired location(s) within the cryoballoon 1030.

Figure 10B:
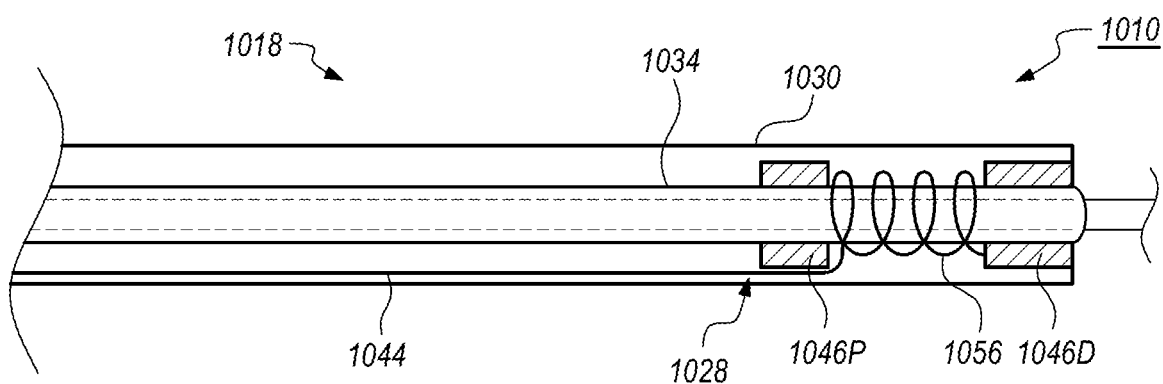
FIG. 10B is a simplified schematic side view illustration of the portion of intravascular catheter system illustrated in FIG. 10A, including the balloon catheter illustrated in the deflated state.

FIG. 10B is a simplified schematic side view illustration of the portion of intravascular catheter system 1010 illustrated in FIG. 10A, including the balloon catheter 1018, shown in the deflated state. In the deflated (or extended) state, because no gap 972 (illustrated in FIG. 9B) exists, the fluid discharge region 1056 is still in substantially the same position relative to the distal fluid injection line stop 1046D and the proximal fluid injection line stop 1046P of the compensation assembly 1028. However, in one embodiment, slight rotational movement of the fluid discharge region 1056 relative to the guidewire lumen 1034 can still occur despite the absence of the gap 972.

With this design, the fluid injection line stops 1046D, 1046P on the guidewire lumen 1034 allow for the fluid discharge region 1056 to freely rotate, thereby reducing a moment arm on the fluid discharge region 1056. Further, likelihood of torqueing the guidewire lumen 1034 unnecessarily is reduced.

It is understood that although a number of different embodiments of the fluid injection line compensation assembly of the intravascular catheter system have been illustrated and described herein, one or more features of any one embodiment can be combined with one or more features of one or more of the other embodiments, provided that such combination satisfies the intent of the present invention.

While a number of exemplary aspects and embodiments of the fluid injection line compensation assembly of the intravascular catheter system have been discussed above, those of skill in the art will recognize certain modifications, permutations, additions and sub-combinations thereof. It is therefore intended that the following appended claims and claims hereafter introduced are interpreted to include all such modifications, permutations, additions and sub-combinations as are within their true spirit and scope.

What is claimed is:

1. A cryoablation catheter comprising:
   a catheter shaft;
   a guidewire lumen disposed within and slidable relative to the shaft;
   a cryoballoon having a first end portion secured to a distal end of the shaft, and a second end portion attached to the guidewire lumen distal to the distal end of the shaft;
   a fluid injection line having a fluid discharge region positioned within the cryoballoon, the fluid discharge region including a fluid port so that cryogenic fluid can be distributed from the fluid injection line to within the cryoballoon, the fluid discharge region being movable relative to the guidewire lumen;
   a proximal fluid injection line stop that is positioned adjacent to the guidewire lumen, the proximal fluid injection line stop being positioned within the cryoballoon;
   a distal fluid injection line stop that is positioned adjacent to the guidewire lumen so that the fluid discharge region is positioned between the proximal fluid injection line stop and the distal fluid injection line stop;
   a handle manifold having a first opening and a second opening spaced from the first opening, wherein the guidewire lumen extends through the first opening and the fluid injection line extends through the second opening; and
   a fluid injection frictional element around the fluid injection line within the second opening, and a guidewire lumen sealer within the first opening forming a seal around the guidewire lumen within the first opening.

2. The cryoablation catheter of claim 1, wherein the fluid discharge region is movable in a longitudinal direction along the guidewire lumen.

3. The cryoablation catheter of claim 2, wherein when the guidewire lumen moves in either a distal or proximal direction, the fluid injection line moves substantially with the guidewire lumen.

4. The cryoablation catheter of claim 1, wherein the fluid discharge region is rotatably movable about the guidewire lumen.

5. The cryoablation catheter of claim 1, wherein at least one of the proximal fluid injection line stop and the distal fluid injection line stop encircles the guidewire lumen.

6. The cryoablation catheter of claim 1, further including a frictional element that frictionally maintains the positioning of the fluid injection line absent movement of the guidewire lumen.

7. A cryoablation catheter comprising:
   a catheter shaft;
   a guidewire lumen disposed within and slidable relative to the shaft;
   a cryoballoon having a first end portion secured to a distal end of the shaft, and a second end portion attached to the guidewire lumen distal to the distal end of the shaft;
   a fluid injection line having a fluid discharge region positioned within the cryoballoon, the fluid discharge region including a fluid port so that cryogenic fluid can, be distributed from the fluid injection line to within the cryoballoon, the fluid discharge region being movable relative to the guidewire lumen; and
   a handle assembly coupled to a proximal end of the shaft and including a handle manifold having a first opening and second opening spaced from the first opening, the guidewire lumen slidably extending through the first opening and the fluid injection line slidably extending through the second opening, and further including a guidewire lumen sealer that forms a seal around the guidewire lumen within the first opening and a fluid injection line frictional element positioned around the fluid injection line within the second opening.

8. The cryoablation catheter of claim 7, wherein the guidewire lumen sealer does not bias the guidewire lumen in either a proximal or a distal direction relative to the cryoballoon.

9. The cryoablation catheter of claim 7 wherein the guidewire lumen sealer includes one or more O-rings disposed within the handle manifold and around the guidewire lumen.

10. The cryoablation catheter of claim 7, wherein the guidewire lumen sealer includes at least one of an electronic actuator, a solenoid, and a set screw.

11. The cryoablation catheter of claim 7, wherein the guidewire lumen sealer can be tuned to vary an amount of friction between the guidewire lumen sealer and the fluid injection line.

12. The cryoablation catheter of claim 7, further comprising a coupler that holds a portion of the fluid injection line adjacent to a portion of the guidewire lumen.

13. The cryoablation catheter of claim 12, wherein the coupler at least partially encircles the fluid injection line and the guidewire lumen.

\* \* \* \* \*